United States Patent [19]

Berg et al.

[11] Patent Number: 5,405,504

[45] Date of Patent: * Apr. 11, 1995

[54] SEPARATION OF 1-DECENE FROM 2-OCTANONE BY AZEOTROPIC DISTILLATION

[75] Inventors: Lloyd Berg, 1314 S. Third Ave., Bozeman, Mont. 59715; Randy W. Wytcherley, Bozeman, Mont.

[73] Assignee: Lloyd Berg, Bozeman, Mont.

[*] Notice: The portion of the term of this patent subsequent to Apr. 4, 2012 has been disclaimed.

[21] Appl. No.: 188,839

[22] Filed: Jan. 31, 1994

[51] Int. Cl.$^6$ .................... B01D 3/36; C07C 7/06
[52] U.S. Cl. .................... 203/57; 203/58; 203/60; 203/62; 203/63; 203/64; 203/66; 568/410; 585/862; 585/864; 585/865; 585/866

[58] Field of Search ............ 203/63, 60, 58, 64, 203/57, 62, 66; 585/860, 862, 864, 865, 866; 568/410

[56] References Cited

U.S. PATENT DOCUMENTS

| | | | |
|---|---|---|---|
| 2,305,236 | 12/1942 | Bruson | 568/440 |
| 5,135,617 | 8/1992 | Brown et al. | 203/63 |
| 5,250,157 | 10/1993 | Berg et al. | 203/68 |
| 5,262,015 | 11/1993 | Berg et al. | 585/862 |

*Primary Examiner*—Wilbur Bascomb, Jr.

[57] ABSTRACT

1-Decene is impossible to separate from 2-octanone by conventional distillation or rectification because the two compounds form a minimum boiling azeotrope. 1-Decene can be readily separated from 2-octanone by azeotropic distillation. Effective agents are 1-propanol, 2-ethoxyethanol, and methanol.

1 Claim, No Drawings

SEPARATION OF 1-DECENE FROM 2-OCTANONE BY AZEOTROPIC DISTILLATION

FIELD OF THE INVENTION

This invention relates to a method for separating 1-decene from 2-octanone using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility of the compounds in a direction to make the separation on each plate greater and thus require either fewer plates to effect the same separation, or make possible a greater degree of separation with the same number of plates. The azeotrope forming agent is introduced with the feed to a continuous column. The azeotrope product and the more volatile component are taken off as overhead product and the less volatile component comes off as bottoms product. The usual methods of separating the azeotrope former from the more volatile component are cooling and phase separation or solvent extraction.

In the Fischer-Tropsch process for converting carbon monoxide and hydrogen into liquids, gases and waxes, hundreds of different hydrocarbons and oxygenated compounds are formed, most of them in very small amounts. One valuable compound occurring in reasonable quantities is 1-decene, n.b.p.=170.6° C. 1-Decene cannot be separated completely due to the presence of a minimum boiling azeotrope with 2-octanone, n.b.p.=173° C., which is also produced in the Fischer-Tropsch process. The azeotrope contains approximately 65% 1-decene and 35% 2-octanone. Azeotropic distillation would be an attractive method of effecting the separation of 1-decene from 2-octanone by rectification.

Since 1-decene and 2-octanone form a minimum boiling azeotrope, their relative volatility is 1.0 and separation by conventional rectification is impossible. Table 1 shows the number of plates required if agents can be found that will increase the relative volatility. A relative volatility of 1.8 will require only 23 plates to obtain 99.54 purity.

TABLE 1

Theoretical and Actual Plates Required vs. Relative Volatility

| Relative Volatility | Theoretical Plates Required At Total Reflux, 99.5% Purity | Actual Plates Required, 75% Efficiency |
| --- | --- | --- |
| 1.02 | 534 | 712 |
| 1.1 | 111 | 148 |
| 1.2 | 58 | 77 |
| 1.4 | 31 | 41 |
| 1.6 | 22 | 29 |
| 1.8 | 18 | 24 |

OBJECTIVE OF THE INVENTION

The object of this invention is to provide a process or method of azeotropic distillation that will enhance the relative volatility of 1-decene from 2-octanone in their separation in a rectification column. It is a further object of this invention to identify organic compounds which in addition to the above constraints, are stable, can be separated from 1-decene in the overhead product and recycled to the azeotrope column and reused with little decomposition.

SUMMARY OF THE INVENTION

The objects of this invention are provided by a process for separating 1-decene from 2-octanone which entails the use of certain organic compounds as the agent in azeotropic distillation.

DETAILED DESCRIPTION OF THE INVENTION

We have discovered that certain organic compounds will greatly improve the relative volatility of 1-decene to 2-octanone and permit the separation of 1-decene from 2-octanone by rectification when employed as the agent in azeotropic distillation. The effective agents are listed in Table 2.

TABLE 2

Effective Extractive Distillation Agents

| Compounds | Relative Volatility (Dec/Oct) | | |
| --- | --- | --- | --- |
| | 80% Dec | 90% Dec | 92% Dec |
| No Agent | 0.8 | 0.7 | 0.8 |
| 1-methoxy-2-propanol | 1.3 | | |
| 1-propanol | 1.5 | 1.8 | |
| 2-butanol | 1.6 | 1.7 | |
| 2-ethoxyethanol | | 1.6 | 2.9 |
| butyl propionate | 1.2 | | |
| dimethyl carbonate | 1.2 | | |
| ethyl acetoacetate | 1.2 | 1.3 | |
| ethylene glycol ethyl ether | 1.5 | | |
| ethylene glycol butyl ether | 1.3 | | |
| methyl ethyl ketoxime | | 1.4 | |
| methyl isoamyl ketone | | 1.3 | |
| methanol | | | 2.5 |
| dimethyl sulfoxide | | | 1.2 |

Presented are the relative volatilities of 1-decene vs. 2-octanone at three different feed compositions, 80% 1-decene, 90% 1-decene, and 92% 1-decene. Since these are different from the azeotropic composition, the relative volatility of the pair is not at 1.0. The relative volatility for the 1-decene - 2-octanone (Dec/Oct) is listed with no agent for comparison purposes. The agents found to be effective at breaking the azeotrope are 1-methoxy-2-propanol, 1-propanol, 2-butanol, 2-ethoxyethanol, butyl propionate, dimethyl carbonate, ethyl acetoacetate, ethylene glycol ethyl ether, ethylene glycol butyl ether, methyl ethyl ketoxime, methyl isoamyl ketone, methanol, and dimethyl sulfoxide.

THE USEFULNESS OF THE INVENTION

The usefulness or utility of this invention can be demonstrated by referring to the data presented in Tables 1 and 2. All of the successful agents show that 1-decene can be separated from 2-octanone by means of azeotropic distillation in a rectification column and that the ease of separation as measured by relative volatility is considerable.

WORKING EXAMPLES

Example 1

Fifty grams of 2-ethoxyethanol was added to a mixture containing 76 grams of 1-decene and 8 grams of 2-octanone, and charged to an Othmer-type vapor-liquid equilibrium still and refluxed for four hours. Analysis of the vapor and liquid by gas chromatography gave a vapor composition of 86.8% 1-decene, 13.2% 2-octanone and a liquid composition of 80.8% 1-decene, 19.2% 2-octanone. This indicates a relative volatility of 1-decene to 2-octanone of 1.6.

Example 2

One hundred and fifty grams of 1-propanol was added to a mixture containing 76 grams of 1-decene and 8 grams of 2-octanone, and charged to the stillpot of a glass perforated plate rectification column containing approximately 7.3 theoretical stages, and refluxed for four hours. Analysis of the vapor and liquid by gas chromatography gave a vapor composition of 99.4% 1-decene, 0.6% 2-octanone and a liquid composition of 92.5% 1-decene, 7.5% 2-octanone. This indicates a relative volatility of 1-decene to 2-octanone of 1.4.

We claim:

1. A method for recovering 1-decene from a mixture containing 1-decene and 2-octanone which comprises distilling the mixture in a rectification column in the presence of an azeotrope forming agent, recovering the 1-decene and the azeotrope forming agent as overhead product and obtaining the 2-octanone as bottoms product, wherein said azeotrope forming agent consists of one material selected from the group consisting of 1-methoxy-2-propanol, 2-butanol, 2-ethoxyethanol, dimethyl carbonate, ethyl acetoacetate, ethylene glycol ethyl ether, ethylene glycol butyl ether, methyl ethyl ketoxime, methyl isoamyl ketone, methanol, and dimethyl sulfoxide.

* * * * *